United States Patent [19]

Lau et al.

[11] Patent Number: 5,457,020
[45] Date of Patent: Oct. 10, 1995

[54] PHOTOGRAPHIC MATERIAL AND PROCESS COMPRISING A BICYCLIC PYRAZOLO COUPLER

[75] Inventors: Philip T. S. Lau; Ping W. Tang; Stanley W. Cowan, all of Rochester, N.Y.

[73] Assignee: Eastman Kodak Company, Rochester, N.Y.

[21] Appl. No.: 992,396

[22] Filed: Dec. 18, 1992

[51] Int. Cl.[6] .................................................. G03C 7/38
[52] U.S. Cl. .......................... 430/558; 430/386; 430/387
[58] Field of Search .................................. 430/558, 386, 430/387

[56] References Cited

FOREIGN PATENT DOCUMENTS

| | | | |
|---|---|---|---|
| 1272743 | 12/1986 | Japan | 430/558 |
| 2092944 | 4/1987 | Japan | 430/558 |
| 3103245 | 5/1988 | Japan | 430/558 |
| 0264753 | 11/1988 | Japan | 430/558 |
| 1066646 | 3/1989 | Japan | 430/558 |

*Primary Examiner*—Lee C. Wright
*Attorney, Agent, or Firm*—Arthur E. Kluegel

[57] ABSTRACT

Novel bicyclic pyrazolo couplers containing a ballast group of formula (I):

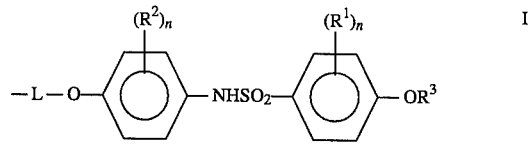

are useful in photographic materials and processes. The couplers exhibit increased coupling activity, and provide formation of dyes having improved maximum magenta image dye density, hue, and dye light stability when employed in color photographic materials and processes.

10 Claims, No Drawings

PHOTOGRAPHIC MATERIAL AND PROCESS COMPRISING A BICYCLIC PYRAZOLO COUPLER

FIELD OF THE INVENTION

This invention relates to novel bicyclic pyrazolo dye-forming couplers, to photographic silver halide materials and processes using such couplers and to the dyes formed therefrom. The couplers contain a fully substituted carbon at the 6-position and a ballast containing an alkoxyphenylsulfonamidoaryloxy group.

BACKGROUND OF THE INVENTION

Color images are customarily obtained in the photographic art by reaction between an oxidation product of a silver halide developing agent and a dye-forming coupler. Pyrazolone couplers are useful for forming magenta dye images; however, such couplers have shortcomings with respect to color reproduction in that the unwanted absorption around 430 nm causes color turbidity. Bicyclic pyrazolo couplers, particularly pyrazolotriazole couplers, represent another class of couplers for this purpose. Examples of bicyclic pyrazolo couplers are described in, for example, U.S. Pat. No. 4,443,536; U.S. Pat. Nos. 1,247,493; 1,252,418; and 1,398,979; and U.S. Pat. Nos. 4,665,015; 4,514,490; 4,621,046, 4,540,654; 4,590,153; 4,822,730 and European Patents 177,765 and 119,860. One class of pyrazolotriazole couplers includes 1H-pyrazolo[3,2c][1,2,4]triazole couplers and another includes 1H-pyrazolo[1,5-b][1,2,4] triazole couplers, such as described in European Patent 177765. While these couplers have a reduced level of unwanted absorption, the conversion of the coupler into an azomethine dye is slow and the maximum attainable density is reduced due to lower coupling efficiency. The aforementioned U.S. Pat. No. 4,822,730 discloses pyrazolotriazoles having a group expressed by the formula —(A)L—B where L represents —N(R)SO$_2$—,—SO$_2$N(R)—, or —N(R)SO$_2$N(R)—. The compounds exemplified contain a methyl or unbranched alkyl group at the 6-position rather that a fully substituted carbon. For example, the following compound is suggested:

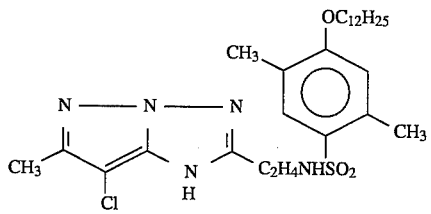

These couplers do not fully satisfy the needs for activity and color reproduction.

Bicyclic pyrazolo couplers containing a t-butyl group at the 6-position are described in U.S. Pat. No. 4,882,266. An example of such a coupler is:

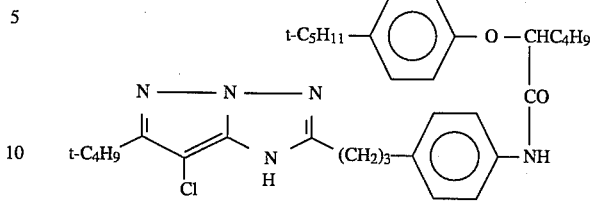

Such couplers suffer from the disadvantage of lower coupling reactivity manifested by lower contrast and Dmax as well as low speeds compared to the corresponding methyl substituted analogs.

Thus, while such magenta dye-forming couplers are useful in photographic silver halide materials and processes, many of such couplers do not have sufficient coupler reactivity. Moreover, the existing products are deficient with respect to dye light stability and color reproduction.

SUMMARY OF THE INVENTION

The present invention provides novel bicyclic pyrazolo couplers, dyes, photographic elements and processes. The photographic elements comprise a support bearing at least one photographic silver halide emulsion layer and a dye-forming bicyclic pyrazolo-based coupler, wherein the dye-forming coupler contains a fully substituted carbon atom at the 6-position and contains at another position a ballast group containing an alkoxyphenylsulfonamidoaryloxy group.

It has been found that photographic elements containing these couplers exhibit increased reactivity and that embodiments show improved dye light stability and color reproduction.

DETAILED DESCRIPTION OF THE INVENTION

Suitably, the couplers of the invention contain a ballast of formula (I):

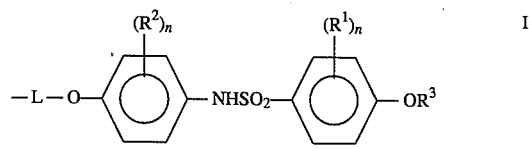

wherein L is a divalent linking group connecting the ballast containing group to the ring; R$^1$ and R$^2$ are independently a substituent with each n being from 0 to 4; and R$^3$ is a substituted or unsubstituted alkyl group of at least 10 carbon atoms. Suitably R$^1$, R$^2$, and R$^3$ may be a substituent group known in the art which typically promotes solubility, diffusion resistance, dye hue, or stability of the dye formed upon reaction of the coupler with the oxidized color developing agent. Preferably they are halogen or an aliphatic residue including a straight or branched alkyl or alkenyl or alkynyl group, a heterocycle, an aralkyl group, a cycloalkyl group or a cycloalkenyl group. The aliphatic residue may be substituted with a substituent bonded through an oxygen atom, a nitrogen atom, a sulfur atom or a carbonyl group, a hydroxy group, an amino group, a nitro group, a carboxy group, an amido group, cyano or halogen. Most preferably they are an alkyl group, an aryl group, a carbonamido group, a sulfonamido group, a sulfone group, a thio group, a sulfoxide group, a ureido group or a multicyclic group.

Preferably, $R^3$ contains from 10 to 21 carbon atoms and most preferably 12 to 18 carbon atoms and may be substituted sike $R^1$ and $R^2$ if desired.

The linking group L is a divalent group. Suitably, L may be an alkylene, arylene, or aryloxylene group of from 1 to 20 carbon atoms An embodiment of the invention is a photographic element comprising a support bearing at least one photographic silver halide emulsion layer and a dye-forming bicyclic pyrazolo coupler wherein the dye-forming coupler contains a ballast of formula (I).

A typical coupler as described is represented by the formula (II):

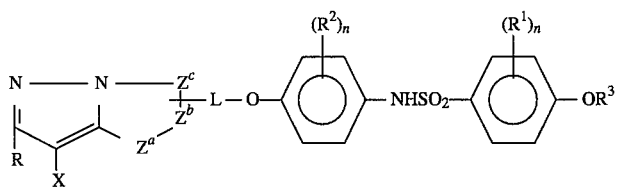

II wherein L, $R^1$ to $R^3$, and n are as described above;

R is a fully substituted carbon atom which is preferably t-butyl, t-amyl, t-octyl, or adamantyl and is most preferably t-butyl or adamantyl;

X is hydrogen or a coupling-off group; and $Z^a$, $Z^b$ and $Z^c$ are independently selected from the group consisting of a substituted or unsubstituted methine group, =N—, =C— or —NH—, provided that one of either the $Z^a$—$Z^b$ bond or the $Z^b$—$Z^c$ bond is a double bond and the other is a single bond, and when the $Z^b$—$Z^c$ bond is a carbon-carbon double bond, it may form part of an aromatic ring, and wherein at least one of $Z^a$, $Z^b$ and $Z^c$ represents a methine group connected with the ballast.

A preferred coupler according to the invention is represented by formula (III)

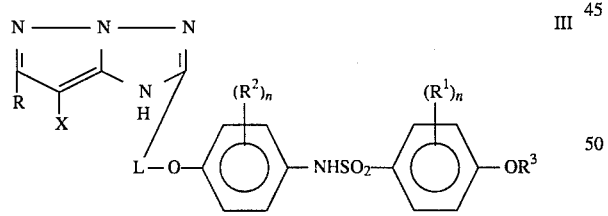

III wherein R, L, $R^1$ to $R^3$, and n are as described above.

Specific examples of couplers useful in the elements of the invention are

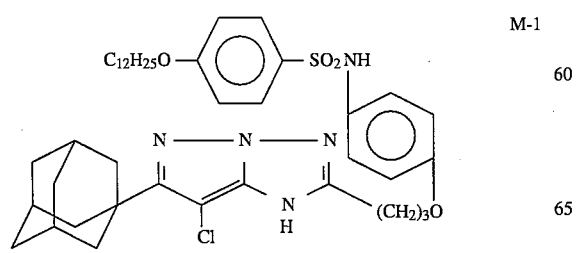

M-1

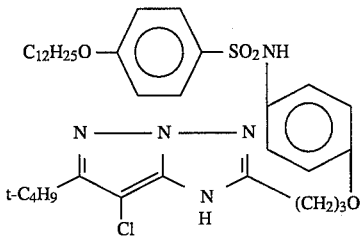

M-2

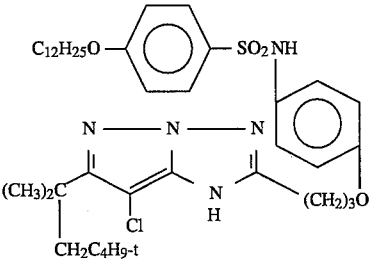

M-3

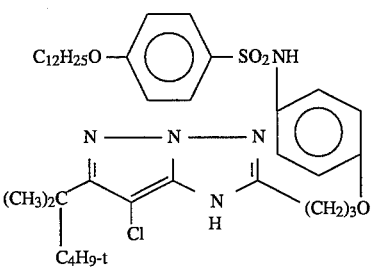

M-4

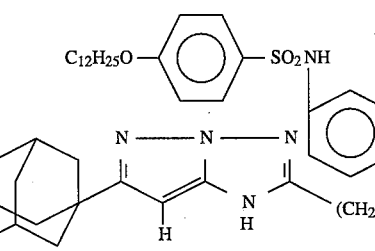

M-5

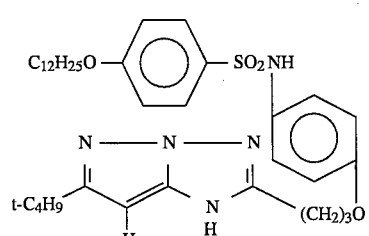

M-6

-continued
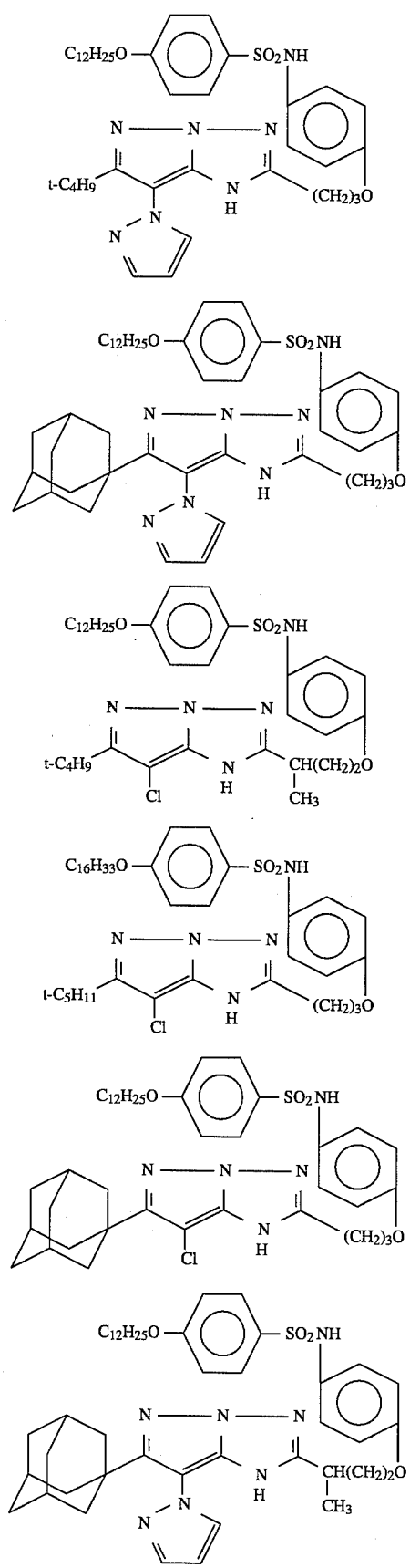
M-7
M-8
M-9
M-10
M-11
M-12
-continued
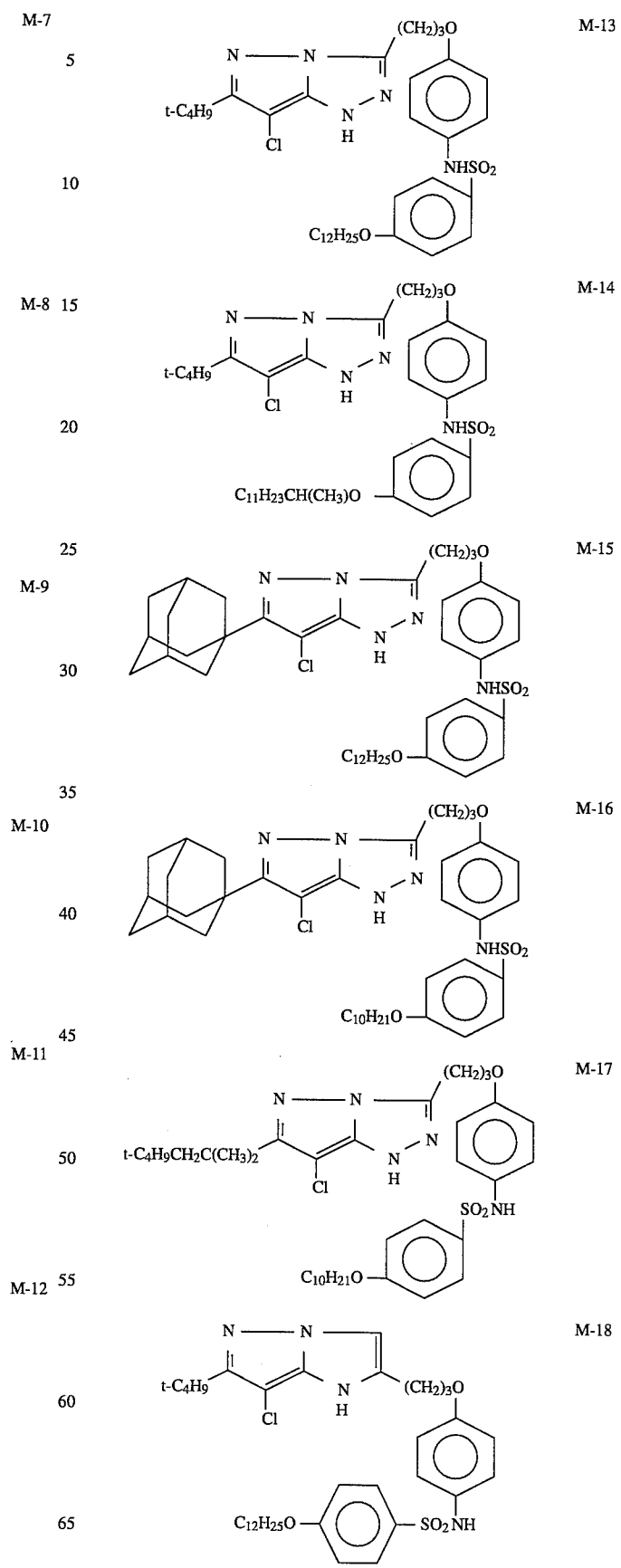
M-13
M-14
M-15
M-16
M-17
M-18

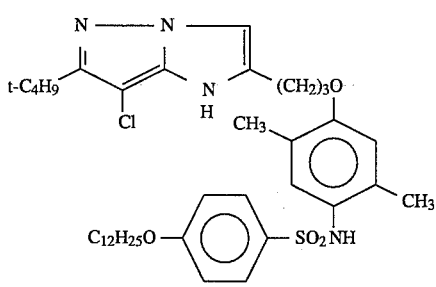

M-19

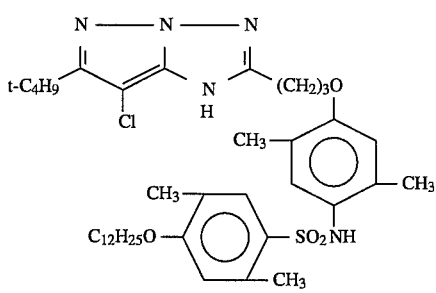

M-20

Examples of substituent groups for $R^1$ to $R^3$ include: an alkyl group which may be straight or branched, and which may be substituted, such as methyl, ethyl, n-propyl, n-butyl, t-butyl, trifluoromethyl, tridecyl or 3—(2,4-di-t-amylphenoxy) propyl; an alkoxy group which may be substituted, such as methoxy or ethoxy; an alkylthio group which may be substituted, such as methylthio or octylthio; an aryl group, an aryloxy group or an arylthio group, each of which may be substituted, such as phenyl, 4-t-butylphenyl, 2,4,6-trimethylphenyl, phenoxy, 2-methylphenoxy, phenylthio or 2-butoxy-5-t-octylphenylthio; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; cyano; an acyloxy group which may be substituted, such as acetoxy or hexadecanoyloxy; a carbamoyloxy group which may be substituted, such as N-phenylcarbamoyloxy or N-ethylcarbamoyloxy; a silyloxy group which may be substituted, such as trimethylsilyloxy; a sulfonyloxy group which may be substituted, such as dodecylsulfonyloxy; an acylamino group which may be substituted, such as acetamido or benzamido; an anilino group which may be substituted, such as phenylanilino or 2-chloroanilino; an ureido group which may be substituted, such as phenylureido or methylureido; an imido group which may be substituted, such as N-succinimido or 3-benzylhydantoinyl; a sulfamoylamino group which may be substituted, such as N,N-dipropyl-sulfamoylamino or N-methyl-N-decylsulfamoylamino.

Additional examples of substituent groups include: a carbamoylamino group which may be substituted, such as N-butylcarbamoylamino or N,N-dimethyl-carbamoylamino; an alkoxycarbonylamino group which may be substituted, such as methoxycarbonylamino or tetradecyloxycarbonylamino; an aryloxycarbonylamino group which may be substituted, such as phenoxycarbonylamino or 2,4-di-t-butylphenoxycarbonylamino; a sulfonamido group which may be substituted, such as methanesulfonamido or hexadecanesulfonamido; a carbamoyl group which may be substituted, such as N-ethylcarbamoyl or N,N-dibutylcarbamoyl; an acyl group which may be substituted, such as acetyl or (2,4-di-t-amylphenoxy)acetyl; a sulfamoyl group which may be substituted such as N-ethylsulfamoyl or N,N-dipropylsulfamoyl; a sulfonyl group which may be substituted, such as methanesulfonyl or octanesulfonyl; a sulfinyl group which may be substituted, such as octanesulfinyl or dodecylsulfinyl; an alkoxycarbonyl group which may be substituted, such as methoxycarbonyl or butyloxycarbonyl; an aryloxycarbonyl group which may be substituted, such as phenyloxycarbonyl or 3-pentadecyloxycrbonyl; an alkenyl group carbon atoms which may be substituted; a carboxyl group which may be substituted; a sulfo group which may be substituted; hydroxyl; an amino group which may be substituted; or a carbonamido group which may be substituted.

Substituents for the above substituted groups include halogen, an alkyl group, an aryl group, an aryloxy group, a heterocyclic or a heterocyclic oxy group, cyano, an alkoxy group, an acyloxy group, a carbamoyloxy group, a silyloxy group, a sulfonyloxy group, an acylamino group, an anilino group, a ureido group, an imido group, a sulfonylamino group, a carbamoylamino group, an alkylthio group, an arylthio group, a heterocyclic thio group, an alkoxycarbonylamino group, an aryloxycarbonylamino group, a sulfonamido group, a carbamoyl group, an acyl group, a sulfamoyl group, a sulfonyl group, a sulfinyl group, an alkoxycarbonyl group, an aryloxycarbonyl group, an alkenyl group, a carboxyl group, a sulfo group, hydroxyl, an amino group or a carbonamido group.

Generally, the above groups and substituents thereof which contain an alkyl group may include an alkyl group having 1 to 16 carbon atoms. The above groups and substituents thereof which contain an aryl group may include an aryl group having 6 to 8 carbon atoms, and the above groups and substituents which contain an alkenyl group may include an alkenyl group having 2 to 6 carbon atoms.

The bicyclic pyrazolo coupler contains in the coupling position, represented by X in formulae (II) and (III), hydrogen or a coupling-off group also known as a leaving group.

Coupling-off groups are known to those skilled in the art. Such groups can determine the equivalency of the coupler, can modify the reactivity of the coupler, or can advantageously affect the layer in which the coupler is coated or other layers in the element by performing, after release from the coupler, such functions as development inhibition, development acceleration, bleach inhibition, bleach acceleration, color correction, and the like. Representative classes of coupling-off groups include halogen, particularly chlorine, bromine, or fluorine, alkoxy, aryloxy, heterocyclyloxy, heterocyclic, such as hydantoin and pyrazolo groups, sulfonyloxy, acyloxy, carbonamido, imido, acyl, heterocyclylimido, thiocyano, alkylthio, arylthio, heterocyclylthio, sulfonamido, phosphonyloxy and arylazo. They are described in, for example, U.S. Pat. Nos. 2,355,169; 3,227,551; 3,432,521; 3,476,563; 3,617,291; 3,880,661; 4,052,212 and 4,134,766 and in U.K. patents and published application numbers 1,466,728; 1,531,927; 1,533,039; 2,006,755A and 2,017,704A; the disclosures of which are incorporated herein by reference.

Examples of specific coupling-off groups are Cl, F, Br, —SCN, —OCH$_3$, —OC$_6$H$_5$, —OCH$_2$C(=O)NHCH$_2$CH$_2$OH, —OCH$_2$C(=O)NHCH$_2$CH$_2$OCH$_3$, —OCH$_2$C(=O)NHCH$_2$CH$_2$OC(=O)OCH$_3$, —NHSO$_2$CH$_3$, —OC(=O)C$_6$H$_5$, —NHC(=O)C$_6$H$_5$, OSO$_2$CH$_3$, —P(=O)(OC$_2$H$_5$)$_2$, —S(CH$_2$)$_2$CO$_2$H,

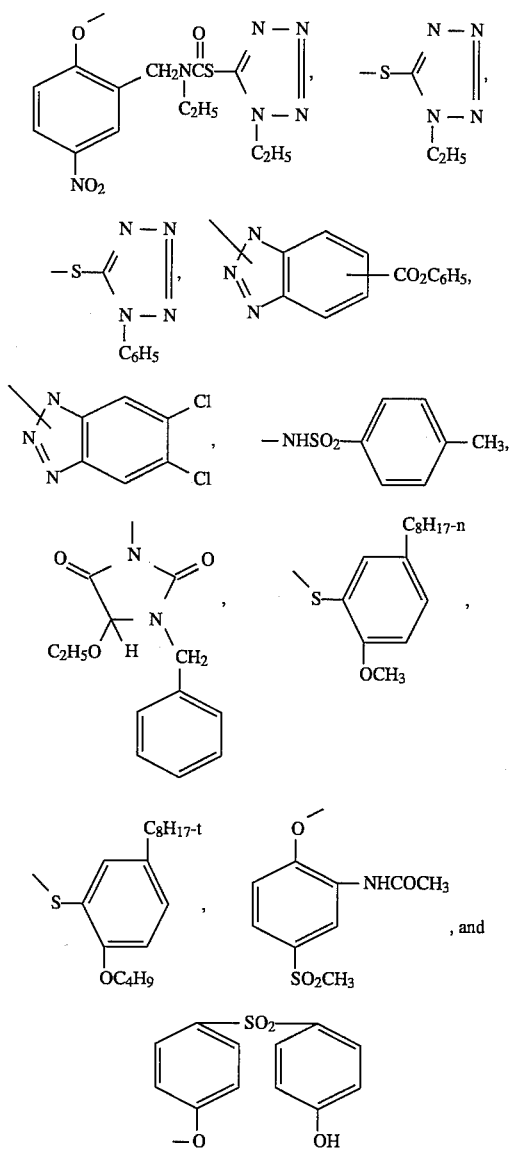

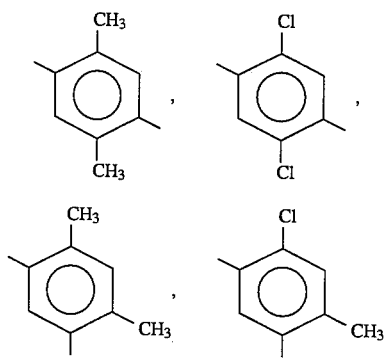

preferably, R' and R" are independently hydrogen or lower alkyl.

Generally, a ballast group is an organic radical of such size and configuration as to confer on the coupler molecule sufficient bulk to render the coupler substantially non-diffusible from the layer in which it is coated in a photographic element. Thus, the combination of groups L, R and $R^1$ to $R^3$ from the formula are chosen to meet this criteria as can be determined by one skilled in the art.

The coupler of this invention can be used in any of the ways and in any of the combinations in which couplers are used in the photographic art. Typically, the coupler is incorporated in a silver halide emulsion and the emulsion coated on a support to form part of a photographic element. Alternatively, the coupler can be incorporated at a location adjacent to the silver halide emulsion where, during development, the coupler will be in reactive association with development products such as oxidized color developing agent. Thus, as used herein, the term "associated" signifies that the coupler is in the silver halide emulsion layer or in an adjacent location where, during processing, the coupler is capable of reacting with silver halide development products.

The photographic elements can be single color elements or multicolor elements. Multicolor elements contain dye image-forming units sensitive to each of the three primary regions of the spectrum. Each unit can comprise a single emulsion layer or multiple emulsion layers sensitive to a given region of the spectrum. The layers of the element, including the layers of the image-forming units, can be arranged in various orders as known in the art. In a alternative format, the emulsions sensitive to each of the three primary regions of the spectrum can be disposed as a single segmented layer.

A typical multicolor photographic element comprises a support bearing a cyan dye image-forming unit comprising at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler, at least one of the couplers in the element being a coupler of this invention. The element can contain additional layers, such as filter layers, interlayers, overcoat layers, subbing layers, and the like.

If desired, the photographic element can be used in conjunction with an applied magnetic layer as described in *Research Disclosure*, November 1992, Item 34390 published by Kenneth Mason Publications, Ltd., Dudley Annex, Preferably, the coupling-off group is H or halogen, and more preferably, H or Cl.

The L group links one of the aryloxy groups to the pyrazolotriazole core. Suitable L groups include the following:

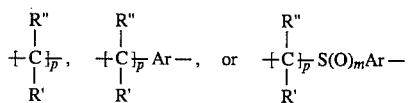

wherein: p1 is an integer of 1–6; m is 0, 1 or 2; R' and R", which may be the same or different, each represents a hydrogen atom or a substituent; and Ar represents a substituted or unsubstituted phenylene group (for example, a 1,4-phenylene group, a 1,3-phenylene group, etc. Representative Ar groups include the following:

12a North Street, Emsworth, Hampshire P010 7DQ, ENGLAND.

In the following discussion of suitable materials for use in the emulsions and elements of this invention, reference will be made to Research Disclosure, December 1989, Item No. 308119, available as described above which will be identified hereafter by the term "Research Disclosure." The contents of the Research Disclosure, including the patents and publications referenced therein, are incorporated herein by reference, and the Sections hereafter referred to are Sections of the Research Disclosure.

The silver halide emulsions employed in the elements of this invention can be either negative-working or positive-working. Suitable emulsions and their preparation as well as methods of chemical and spectral sensitization are described in Sections I through IV. Color materials and development modifiers are described in Sections V and XXI. Vehicles are described in Section IX, and various additives such as brighteners, antifoggants, stabilizers, light absorbing and scattering materials, hardeners, coating aids, plasticizers, lubricants and matting agents are described, for example, in Sections V, VI, VIII, X, XI, XII, and XVI. Manufacturing methods are described in Sections XIV and XV, other layers and supports in Sections XIII and XVII, processing methods and agents in Sections XIX and XX, and exposure alternatives in Section XVIII.

Preferred color developing agents are p-phenylenediamines. Especially preferred are:

4-amino N,N-diethylaniline hydrochloride, 4-amino-3-methyl-N,N-diethylaniline hydrochloride, 4-amino-3-methyl-N-ethyl-N-(b-(methanesulfonamido) ethyl)aniline sesquisulfate hydrate, 4-amino-3-methyl-N-ethyl-N-(b-hydroxyethyl)aniline sulfate, 4-amino-3-b-(methanesulfonamido)ethyl-N,N-diethylaniline hydrochloride and 4-amino-N-ethyl-N-(2-methoxyethyl)-m-toluidine di-p-toluene sulfonic acid.

With negative working silver halide a negative image can be formed. Optionally positive (or reversal) image can be formed.

Coupling-off groups are well known in the art. Such groups can determine the equivalency of the coupler, i.e., whether it is a 2-equivalent or a 4-equivalent coupler, or modify the reactivity of the coupler. Such groups can advantageously affect the layer in which the coupler is coated, or other layers in the photographic recording material, by performing, after release from the coupler, functions such as dye formation, development acceleration or inhibition, bleach acceleration or inhibition, electron transfer facilitation, color correction and the like.

Representative classes of coupling-off groups include chloro, alkoxy, aryloxy, heteroyloxy, sulfonyloxy, acyloxy, acyl, heterocyclyl, sulfonamido, mercaptotetrazole, mercaptopropionic acid, phosphonyloxy anylthio, and arylazo. These coupling-off groups are described in the art, for example, in U.S. Pat. Nos. 2,455,169, 3,227,551, 3,432,521, 3,476,563, 3,617,291, 3,880,661, 4,052,212 and 4,134,766and in U.K. Patents and published application Nos. 1,466,728, 1,531,927, 1,533,039, 2,006,755A and 2,017,704A, the disclosures of which are incorporated herein by reference.

The magenta coupler described herein may be used in combination with other types of magenta image couplers such as 3-acylamino- or 3-anilino-, 5-pyrazolones and heterocyclic couplers (e.g. pyrazoloazoles) such as those described in EP 285,274 U.S. Pat. No. 4,540,654EP 119,860, or with other 5-pyrazolone couplers containing different ballasts or coupling-off groups such as those described in U.S. Pat. No. 4,301,235U.S. Pat. No. 4,853,319 and U.S. Pat. No. 4,351,897. The coupler may also be used in association with yellow or cyan colored couplers (e.g. to adjust levels of interlayer correction) and with masking couplers such as those described in EP 213.490: Japanese Published Application 58-172,647; U.S. Pat. No. 2,983,608; German Application DE 2,706,117C; U.K. Patent 1,530, 272; Japanese Application A-113935; U.S. Pat. No. 4,070, 191 and German Application DE 2,643,965. The masking couplers may be shifted or blocked.

For example, the magenta coupler of the invention may be used to replace all or part of the magenta layer image coupler or may be added to one or more of the other layers in a color negative photographic element comprising a support bearing the following layers from top to bottom:

(1) one or more overcoat layers containing ultraviolet absorber(s);

(2) a two-coat yellow pack with a fast yellow layer containing "Coupler 1": Benzoic acid, 4-chloro-3-((2-(4-ethoxy-2,5-dioxo-3-(phenylmethyl)-1-imidazolidinyl)-3-(4-methoxyphenyl)-1,3-dioxopropyl)amino)-, dodecyl ester and a slow yellow layer containing the same compound together with "Coupler 2": Propanoic acid, 2-[[5-[[4-[2-[[[2,4-bis( 1,1-dimethylpropyl)phenoxy]acetyl]amino]-5[(2,2,3,3,4,4,4-heptafluoro-1-oxobutyl)amino]-4-hydroxyphenoxy]-2,3-dihydroxy-6-[(propylamino)carbonyl]phenyl]thio]-1,3,4-thiadiazol-2-yl]thio]-, methyl est and "Coupler 3": 1-((dodecyloxy)carbonyl) ethyl (3-chloro-4-((3-(2-chloro-4-((1-tridecanoylethoxy) carbonyl)anilino) -3-oxo-2-((4)(5)(6) -(phenoxycarbonyl)-1H-benzotriazol-1-yl)propanoyl)amino))benzoate;

(3) an interlayer containing fine metallic silver;

(4) a triple-coat magenta pack with a fast magenta layer containing "Coupler 4": Benzamide, 3-((2-(2,4-bis(1, 1-dimethylpropyl)phenoxy)-1-oxobutyl)amino)-N-(4, 5-dihydro-5-oxo-1-(2,4,6-trichlorophenyl)-1H-pyrazol-3-yl)-, "Coupler 5": Benzamide, 3-((2-(2,4-bis(1,1-dimethylpropyl)phenoxy)-1-oxobutyl)amino)-N(4',5'-dihydro-5'-oxo-1'-(2,4,6-trichlorophenyl) (1,4'-bi-1H-pyrazol)-3'-yl)-, "Coupler 6": Carbamic acid, (6-(((3-(dodecyloxy)propyl) amino)carbonyl)-5-hydroxy-1-naphthalenyl)-, 2-methylpropyl ester , "Coupler 7": Acetic acid, ((2-((3-(((3-(dodecyloxy)propyl)amino) carbonyl)-4-hydroxy-8-(((2-methylpropoxy) carbonyl) amino) -1-naphthalenyl)oxy)ethyl)thio) -, and "Coupler 8" Benzamide, 3-((2-(2,4-bis (1,1-dimethylpropyl) phenoxy)-1-oxobutyl)amino)-N-(4,5-dihydro-4-((4-methoxyphenyl azo)-5-oxo-1-(2,4,6-trichlorophenyl)-1H-pyrazol-3-yl)-; a mid-magenta layer and a slow magenta layer each containing "Coupler 9": 2-Propenoic acid , butyl ester, styrene, 2:1:1 polymer with (N[1-(2,4,6-trichlorophenyl 4,5 -dihydro-5-oxo-1H-pyrazol-3-yl ]-2-methyl-2-propenamide)$_2$ and "Coupler 10": Tetradecanamide, N-(4-chloro-3-((4-((4-((2, 2-dimethyl1-oxopropyl) amino) phenyl)azo)-4,5-dihydro-5-oxo-1(2,4,6-trichlorophenyl)- 1H-pyrazol-3-yl)amino)phenyl)-, in addition to Couplers 3 and 8;

(5) an interlayer;

(6) a triple-coat cyan pack with a fast cyan layer containing Couplers 6 and 7; a mid-cyan containing Coupler 6 and "Coupler 11": 2,7-Naphthalenedisulfonic acid, 5-(acetylamino)-3-((4-(2-((3-(((3-(2,4-bis(1,1-dimethylpropyl)phenoxy) propyl)amino)carbonyl)-4-hydroxy-1-naphthalenyl) oxy) ethoxy)phenyl)azo)-4-hydroxy-, disodium salt; and a slow cyan layer containing Couplers 2 and 6;

(7) an undercoat layer containing Coupler 8; and (8) an antihalation layer.

In a color paper format, the magenta coupler of the invention may suitably be used to replace all or a part of the magenta coupler in a photographic element such as one comprising a support bearing the following from top to bottom:

(1) one or more overcoats;

(2) a cyan layer containing "Coupler 1": Butanamide, 2-(2,4-bis(1,1-dimethylpropyl)phenoxy)-N-(3,5-dichloro-2-hydroxy-4-methylphenyl) -, "Coupler 2 ": Acetamide, 2-(2,4-bis(1,1-dimethylpropyl)phenoxy)-N-(3,5-dichloro-2-hydroxy-4-, and UV Stabilizers: Phenol, 2-(5-chloro-2H-benzotriazol-2-yl) -4,6-bis(1,1-dimethylethyl)-;Phenol, 2-(2H-benzotriazol-2-yl)-4-(1,1-dimethylethyl)-;Phenol, 2-(2H-benzotriazol-2-yl) -4(1,1-dimethylethyl)- 6-(1-methylpropyl) -; and Phenol, 2-(2H-benzotriazol-2-yl)-4,6-bis(1,1-dimethylpropyl)- and a poly(t-butylacrylamide) dye stabilizer;

(3) an interlayer;

(4) a magenta layer containing "Coupler 3": Octanamide, 2-[2,4-bis(1,1-dimethylpropyl)phenoxy]-N-[2-(7-chloro-6-methyl- 1H-pyrazol[1,5-b][1,2,4]triazol-2-yl-)propyl]- together with 1,1'-Spirobi(1H-indene), 2,2', 3,3'-tetrahydro-3,3,3', 3'-tetramethyl-5,5', 6,6'-tetrapropoxy-;

(5) an interlayer; and (6) a yellow layer containing "Coupler 4": 1-Imidazolidineacetamide, N-(5-((2-(2,4-bis(1,1-dimethylpropyl)phenoxy)-1-oxobutyl)amino)- 2chlorophenyl)-.alpha.-(2,2-dimethyl- 1-oxopropyl) -4-ethoxy-2,5-dioxo-3-(phenylmethyl)-.

In a reversal medium, the magenta coupler of the invention could be used to replace all or part of the magenta coupler in a photographic element such as one comprising a support and bearing the following layers from top to bottom:

(1) one or more overcoat layers;

(2) a nonsensitized silver halide containing layer;

(3) a triple-coat yellow layer pack with a fast yellow layer containing "Coupler 1": Benzoic acid, 4-(1-(((2-chloro-5-((dodecylsulfonyl)amino)phenyl) amino)carbonyl)-3,3-dimethyl-2-oxobutoxy)-, 1-methylethyl ester; a mid yellow layer containing Coupler 1and "Coupler 2": Benzoic acid, 4-chloro-3-[[2-[4-ethoxy-2,5-dioxo-3-(phenylmethyl)-1-imidazolidinyl]- 4,4-dimethyl-1,3-dioxopentyl]amino]-, dodecylester; and a slow yellow layer also containing Coupler 2;

(4) an interlayer;

(5) a layer of fine-grained silver;

(6) an interlayer;

(7) a triple-coated magenta pack with a fast magenta layer containing "Coupler 3": 2-Propenoic acid, butyl ester, polymer with N-[1-(2,5-dichlorophenyl)-4,5-dihydro-5-oxo-1H-pyrazol-3-yl]-2-methyl-2-propenamide; "Coupler 4": Benzamide, 3-((2-(2,4-bis(1,1-dimethylpropyl)phenoxy)-1-oxobutyl)amino)-N-(4,5-dihydro-5-oxo-1-(2,4,6-trichlorophenyl)-1H-pyrazol-3-yl)-; and "Coupler 5": Benzamide, 3-(((2,4-bis(1,1-dimethylpropyl)phenoxy)acetyl)amino)-N-(4,5-dihydro-5-oxo- 1-(2,4,6-trichlorophenyl)-1H-pyrazol-3-yl)-; and containing the stabilizer 1,1'-Spirobi(1H-indene), 2,2', 3,3'-tetrahydro-3,3,3',3'-tetramethyl-5,5',6,6'-tetrapropoxy-; and in the slow magenta layer Couplers 4 and 5 with the same stabilizer;

(8) one or more interlayers possibly including fine-grained nonsensitized silver halide;

(9) a triple-coated cyan pack with a fast cyan layer containing "Coupler 6": Tetradecanamide, 2-(2-cyanophenoxy)-N-(4-((2,2,3,3,4,4,4-heptafluoro- 1-oxobutyl)amino)-3-hydroxyphenyl)-; a mid cyan containing"Coupler 7": Butanamide, N-(4-((2-(2,4-bis (1,1-dimethylpropyl)phenoxy)-1-oxobutyl)amino-2-hydroxyphenyl)-2,2,3,3,4,4,4-heptafluoro- and "Coupler 8": Hexanamide, 2-(2,4-bis (1,1-dimethylpropyl)phenoxy)-N-(4-((2,2,3,3,4,4,4-heptafluoro-1-oxobutyl)amino)-3-hydroxyphenyl) -;

(10) one or more interlayers possibly including fine-grained nonsensitized silver halide; and

(11) an antihalation layer.

The couplers may also be used in association with materials that accelerate or otherwise modify the processing steps e.g. of bleaching or fixing to improve the quality of the image. Bleach accelerators described in EP 193,389; EP 301,477U.S. Pat. Nos. 4,163,669; 4,865,956; and 4,923,784 are particularly useful. Also contemplated is use of the coupler in association with nucleating agents, development accelerators or their precursors (UK Patent 2,097,140; U.K. Patent 2,131,188); electron transfer agents (U.S. Pat. Nos. 4,859,578; 4,912,025); antifogging and anti color-mixing agents such as derivatives of hydroquinones, aminophenols, amines, gallic acid; catechol; ascorbic acid; hydrazides; sulfonamidophenols; and non color-forming couplers.

The couplers may also be used in combination with filter dye layers comprising colloidal silver sol or yellow and/or magenta filter dyes, either as oil-in-water dispersions, latex dispersions or as solid particle dispersions. Additionally, they may be used with "smearing" couplers (e.g. as described in U.S. Pat. No. 4,366,237; EP 96,570; U.S. Pat. Nos. 4,420,556; and 4,543,323.) Also, the couplers may be blocked or coated in protected form as described, for example, in Japanese Application 61/258,249 or U.S. Pat. No. 5,019,492.

The coupler may further be used in combination with image-modifying compounds such as "Developer Inhibitor-Releasing" compounds (DIR's). DIR's useful in conjunction with the couplers of the invention are known in the art and examples are described in U.S. Pat. Nos. 3,137,578; 3,148,022; 3,148,062; 3,227,554; 3,384,657; 3,379,529; 3,615,506; 3,617,291; 3,620,746; 3,701,783; 3,733,201; 4,049,455; 4,095,984; 4,126,459; 4,149,886; 4,150,228; 4,211,562; 4,248,962; 4,259,437; 4,362,878; 4,409,323; 4,477,563; 4,782,012; 4,962,018; 4,500,634; 4,579,816; 4,607,004; 4,618,571; 4,678,739; 4,746,600; 4,746,601; 4,791,049; 4,857,447; 4,865,959; 4,880,342; 4,886,736; 4,937,179; 4,946,767; 4,948,716; 4,952,485; 4,956,269; 4,959,299; 4,966,835; 4,985,336 as well as in patent publications GB 1,560,240; GB 2,007,662; GB 2,032,914; GB 2,099,167; DE 2,842,063, DE 2,937,127; DE 3,636,824DE 3,644,416 as well as the following European Patent Publications: 272,573; 335,319; 336,411; 346, 899; 362, 870; 365,252; 365,346; 373,382; 376,212; 377,463; 378,236; 384,670; 396,486; 401,612; 401,613.

Such compounds are also disclosed in "Developer-Inhibitor-Releasing (DIR) Couplers for Color Photography," C. R. Barr, J. R. Thirtle and P. W. Vittum in *Photographic Science and Engineering*, Vol. 13, p. 174 (1969), incorporated herein by reference. Generally, the developer inhibitor-releasing (DIR) couplers include a coupler moiety and an inhibitor coupling-off moiety (IN). The inhibitor-releasing couplers may be of the time-delayed type (DIAR couplers) which also include a timing moiety or chemical switch which produces a delayed release of inhibitor. Examples of typical inhibitor moieties are: oxazoles, thiazoles, diazoles, triazoles, oxadiazoles, thiadiazoles, oxathiazoles, thiatriazoles, benzotriazoles, tetrazoles, benzimidazoles, indazoles, isoindazoles, mercaptotetrazoles, selenotetrazoles, mercaptobenzothiazoles, selenobenzothiazoles, mercaptobenzoxazoles, selenobenzoxazoles, mercaptobenzimidazoles, selenobenzimidazoles, benzodiazoles, mercaptooxazoles, mercaptothiadiazoles, mercaptothiazoles, mercaptotriazoles, mercaptooxadiazoles, mercaptodiazoles, mercaptooxathiazoles, telleurotetrazoles or benzisodiazoles. In a preferred embodiment, the inhibitor moiety or group is selected from the following formulas:

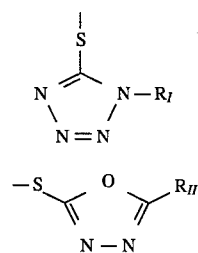

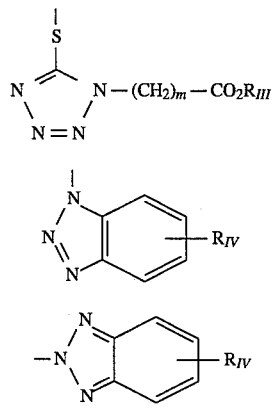

wherein $R_I$ is selected from the group consisting of straight and branched alkyls of from 1 to about 8 carbon atoms, benzyl and phenyl groups and said groups containing at least one alkoxy substituent; $R_{II}$ is selected from $R_I$ and —$SR_I$; $R_{III}$ is a straight or branched alkyl group of from 1 to about 5 carbon atoms and m is from 1 to 3; and $R_{IV}$ is selected from the group consisting of hydrogen, halogens and alkoxy, phenyl and carbonamido groups, —$COOR_V$ and —NHCO-$OR_V$ wherein $R_V$ is selected from substituted and unsubstituted alkyl and aryl groups.

Although it is typical that the coupler moiety included in the developer inhibitor-releasing coupler forms an image dye corresponding to the layer in which it is located, it may also form a different color as one associated with a different film layer. It may also be useful that the coupler moiety included in the developer inhibitor-releasing coupler forms colorless products and/or products that wash out of the photographic material during processing (so-called "universal" couplers).

As mentioned, the developer inhibitor-releasing coupler may include a timing group which produces the time-delayed release of the inhibitor group such as groups utilizing the cleavage reaction of a hemiacetal (U.S. Pat. No. 4,146,396, Japanese Applications 60-249148; 60-249149); groups using an intramolecular nucleophilic substitution reaction (U.S. Pat. No. 4,248,962); groups utilizing an electron transfer reaction along a conjugated system (U.S. Pat. No. 4,409,323; 4,421,845; Japanese Applications 57-188035; 58-98728; 58-209736; 58-209738) groups utilizing ester hydrolysis (German Patent Application (OLS) No. 2,626,315; groups utilizing the cleavage of imino ketals (U.S. Pat. No. 4,546,073); groups that function as a coupler or reducing agent after the coupler reaction (U.S. Pat. Nos. 4,438,193; 4,618,571) and groups that combine the features describe above. It is typical that the timing group or moiety is of one of the formulas:

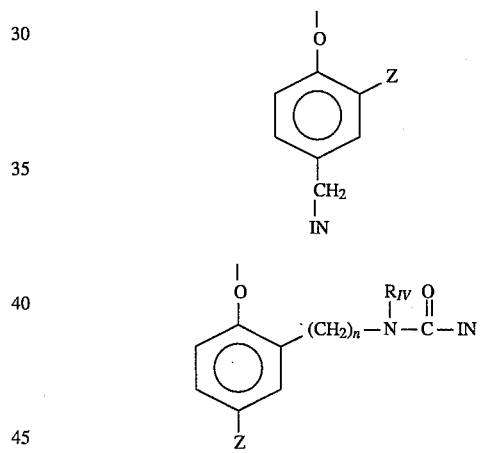

wherein IN is the inhibitor moiety, Z is selected from the group consisting of nitro, cyano, alkylsulfonyl; sulfamoyl (—$SO_2NR_2$); and sulfonamido (—$NRSO_2R$) groups; n is 0 or 1; and $R_{VI}$ is selected from the group consisting of substituted and unsubstituted alkyl and phenyl groups. The oxygen atom of each timing group is bonded to the coupling-off position of the respective coupler moiety of the DIAR.

Suitable developer inhibitor-releasing couplers for use in the present invention include, but are not limited to, the following:

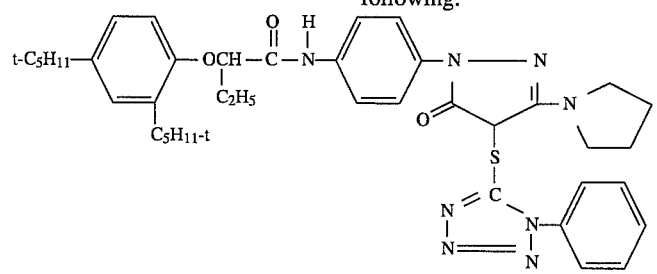

D1

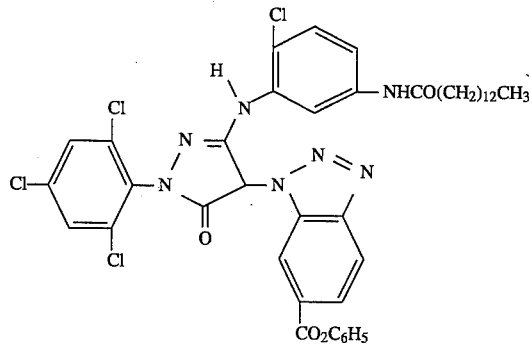
D2

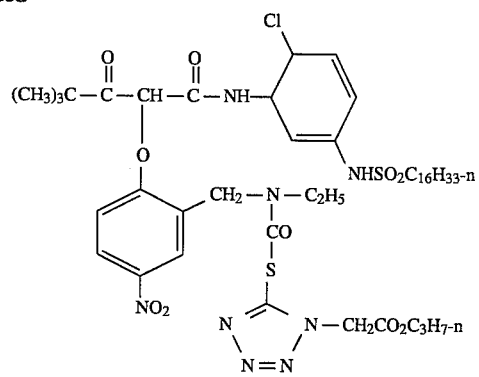
D3

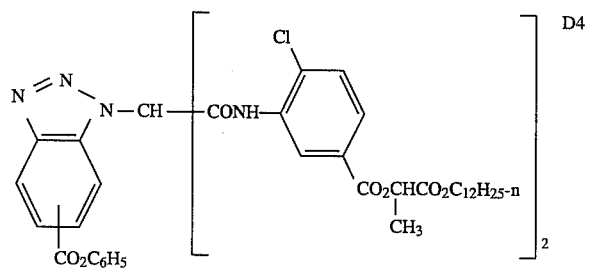
D4

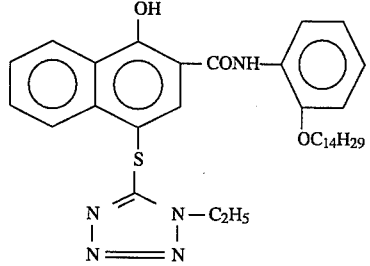
D5

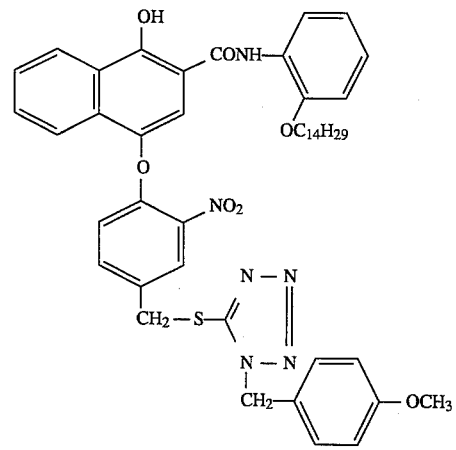
D6

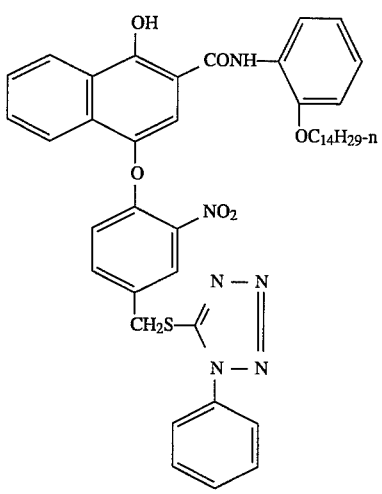
D7

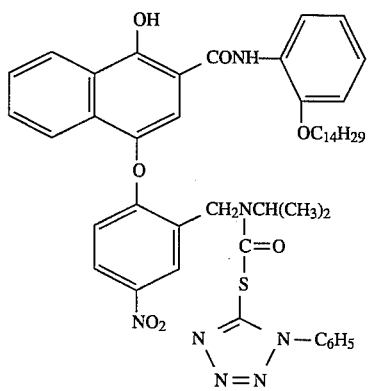
D8

It is also contemplated that the concepts of the present invention may be employed to obtain reflection color prints as described in *Research Disclosure*, November 1979, Item 18716, available from Kenneth Mason Publications, Ltd, Dudley Annex, 12a North Street, Emsworth, Hampshire P0101 7DQ, England, incorporated herein by reference. Materials of the invention may be coated on pH adjusted support as described in U.S. Pat. No. 4,917,994; with epoxy solvents (EP 0 164 961); with nickel complex stabilizers (U.S. Pat. Nos. 4,346,165; 4,540,653 and 4,906,559 for example); with ballasted chelating agents such as those in U.S. Pat. No. 4,994,359 to reduce sensitivity to polyvalent cations such as calcium; and with stain reducing compounds such as described in U.S. Pat. Nos. 5,068,171 and 5,096,805. Other compounds useful in combination with the invention are disclosed in Japanese Published Applications 83-09,959; 83-62,586; 90-072,629, 90-072,630; 90-072,632; 90-072,633; 90-072,634; 90-077,822; 90-078,229; 90-078,230; 90-079,336; 90-079,338; 90-079,690; 90-079,691; 90-080,487; 90-080,489; 90-080,490; 90-080,491; 90-080,492; 90-080,494; 90-085,928; 90-086,669; 90-086,670; 90-087,361; 90-087,362; 90-087,363; 90-087,364; 90-088,096; 90-088,097; 90-093,662; 90-093,663; 90-093,664; 90-093,665; 90-093,666; 90-093,668; 90-094,055; 90-094,056; 90-101,937; 90-103,409; 90-151,577.

Especially useful in this invention are tabular grain silver halide emulsions. Specifically contemplated tabular grain emulsions are those in which greater than 50 percent of the total projected area of the emulsion grains are accounted for by tabular grains having a thickness of less than 0.3 micron (0.5 micron for blue sensitive emulsion) and an average tabularity (T) of greater than 25 (preferably greater than 100), where the term "tabularity" is employed in its art recognized usage as $$T=ECD/t^2$$

where

ECD is the average equivalent circular diameter of the tabular grains in microns and t is the average thickness in microns of the tabular grains.

The average useful ECD of photographic emulsions can range up to about 10 microns, although in practice emulsion ECD's seldom exceed about 4 microns. Since both photographic speed and granularity increase with increasing ECD's, it is generally preferred to employ the smallest tabular grain ECD's compatible with achieving aim speed requirements.

Emulsion tabularity increases markedly with reductions in tabular grain thickness. It is generally preferred that aim tabular grain projected areas be satisfied by thin (t<0.2 micron) tabular grains. To achieve the lowest levels of granularity it is preferred that aim tabular grain projected areas be satisfied with ultrathin (t<0.06 micron) tabular grains. Tabular grain thicknesses typically range down to about 0.02 micron. However, still lower tabular grain thicknesses are contemplated. For example, Daubendiek et al U.S. Pat. No. 4,672,027 reports a 3 mole percent iodide tabular grain silver bromoiodide emulsion having a grain thickness of 0.017 micron.

As noted above tabular grains of less than the specified thickness account for at least 50 percent of the total grain projected area of the emulsion. To maximize the advantages of high tabularity it is generally preferred that tabular grains satisfying the stated thickness criterion account for the highest conveniently attainable percentage of the total grain projected area of the emulsion. For example, in preferred emulsions tabular grains satisfying the stated thickness criteria above account for at least 70 percent of the total grain projected area. In the highest performance tabular grain emulsions tabular grains satisfying the thickness criteria above account for at least 90 percent of total grain projected area.

Suitable tabular grain emulsions can be selected from among a variety of conventional teachings, such as those of the following: Research Disclosure, Item 22534, January 1983, published by Kenneth Mason Publications, Ltd., Emsworth, Hampshire P010 7DD, England; U.S. Pat. Nos. 4,439,520; 4,414,310; 4,433,048; 4,643,966; 4,647,528; 4,665,012; 4,672,027; 4,678,745; 4,693,964; 4,713,320; 4,722,886; 4,755,456; 4,775,617; 4,797,354; 4,801,522; 4,806,461; 4,835,095; 4,853,322; 4,914,014; 4,962,015; 4,985,350; 5,061,069 and 5,061,616.

The emulsions can be surface-sensitive emulsions, i.e., emulsions that form latent images primarily on the surfaces of the silver halide grains, or internal latent images predominantly in the interior of the silver halide grains. The emulsions can be negative-working emulsions, such as surface-sensitive emulsions or unfogged internal latent image-forming emulsions, or direct-positive emulsions of the unfogged, internal latent image-forming type, which are positive-working when development is conducted with uniform light exposure or in the presence of a nucleating agent.

Photographic elements can be exposed to actinic radiation, typically in the visible region of the spectrum, to form a latent image and then processed to form a visible dye image. Processing to form a visible dye image includes the step of contacting the element with a color developing agent to reduce developable silver halide and oxidize the color developing agent. Oxidized color developing agent in turn reacts with the coupler to yield a dye.

With negative-working silver halide, the processing step described above provides a negative image. The described elements can be processed in the known C-41 color process as described in, for example, the British Journal of Photography Annual of 1982, pages 209–211 and 1988, pages 191–198 or in known processes for processing color photographic papers, such as the known RA-4 process of Eastman Kodak Company. The described elements are optionally processed in the known color processes for processing color print papers, such as the processes described in the British Journal of Photography Annual of 1988, pages 198–199. To provide a positive (or reversal) image, the color development step can be preceded by development with a non-chromogenic developing agent to develop exposed silver halide, but not form dye, and then uniformly fogging the element to render unexposed silver halide, but not form dye, and then uniformly fogging the element to render unexposed silver halide developable. Alternatively, a direct positive emulsion can be employed to obtain a positive image.

Development is followed by the conventional steps of bleaching, fixing, or bleach-fixing, to remove silver or silver halide, washing, and drying.

Suitable stabilizers for the photographic elements of this invention include the following:

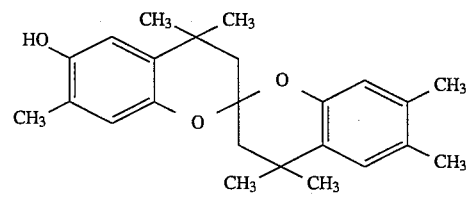

S-1

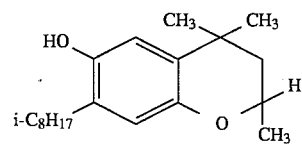

S-2

-continued
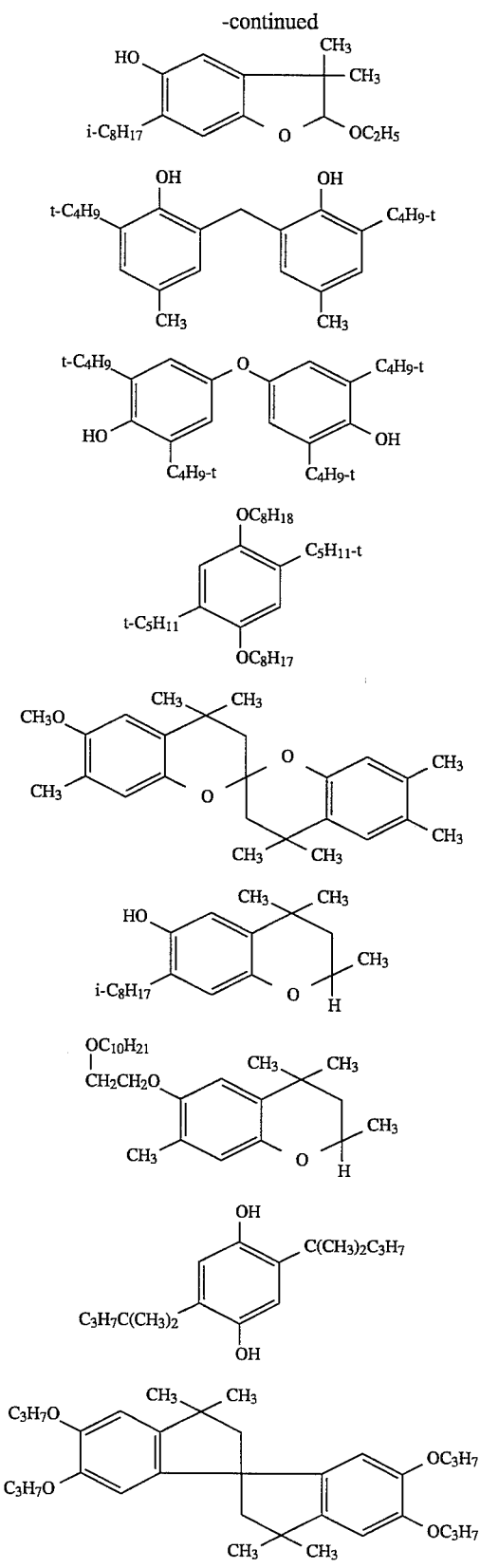
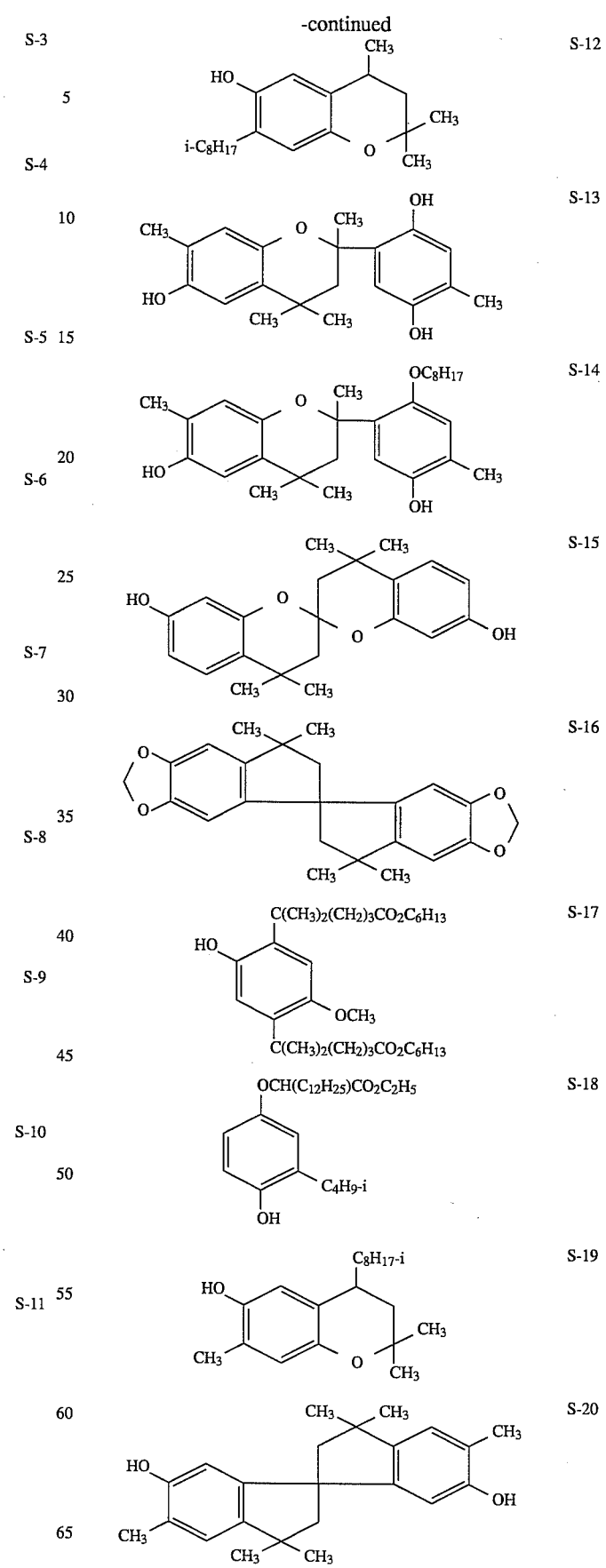

The following examples further illustrate the invention.

Pyrazolotriazole couplers as described are prepared by general methods of synthesis described in the art, such as in U.S. Pat. No. 4,540,654. An illustrative scheme is as follows:

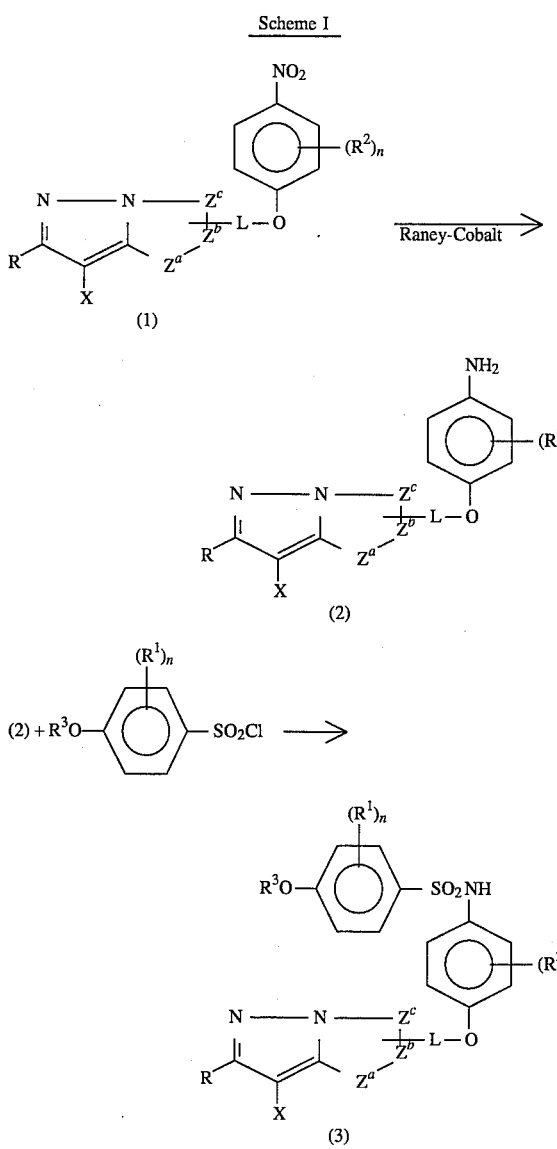

SYNTHESIS EXAMPLE—COUPLER M-1

An example of synthesis of a coupler as described is as follows:

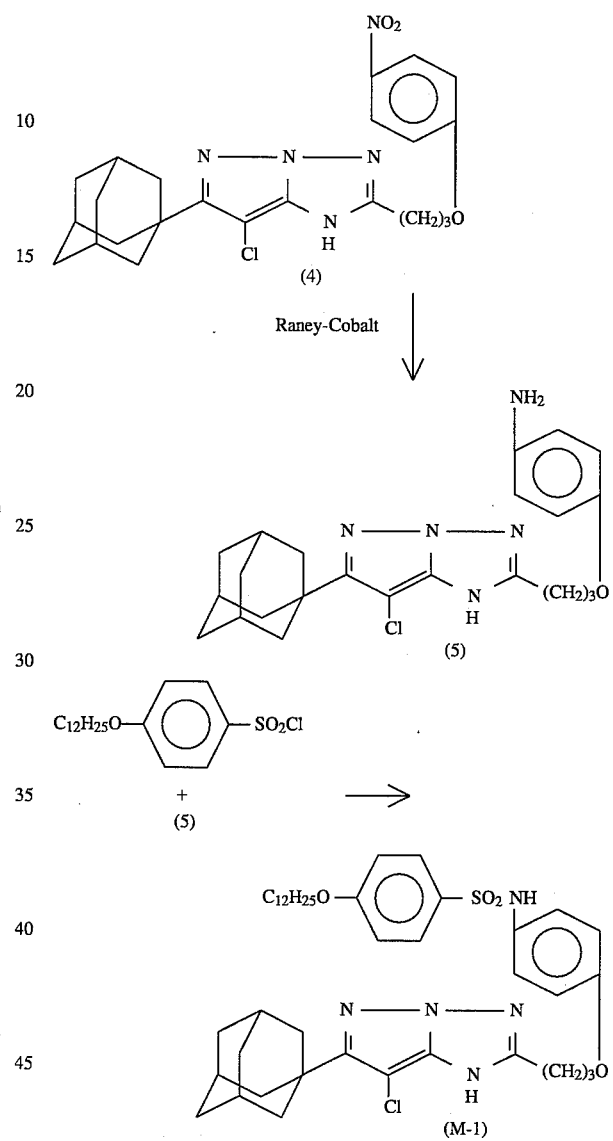

The couplers according to this invention can be prepared by following the general Scheme I as illustrated for Coupler M-1

Preparation of the coupler-amine 125.8 g (0.276 mol) of nitro-compound (4) dissolved in dry tetrahydrofuran was reduced to the corresponding amine using Raney Cobalt as catalyst. The reaction mixture was filtered and concentrated in vacuo to yield 84.6 g (72%) of coupler amine (5) as a tan solid. Physical and spectroscopic data of the amine were consistent with the assigned structure.

Preparation of the Coupler (M-1)

A mixture of 4.26 g (0.01 mol) of coupler-amine (5) and 30 ml of pyridine was stirred and cooled to 5° C., followed by the portionwise addition of 3.61 g (0.01 mol) of 4-dodecyloxybenzenesulfonyl chloride. The reaction was allowed to warm up to room temperature and stirred overnight. The reaction mixture was poured into a mixture of ice-water containing 30 ml of concentrated hydrochloric acid. The mixture was stirred for 0.5 hr and extracted with three 250 ml portions of ethyl acetate. The combined extracts were washed with two 100 ml portions of water, dried over anhydrous magnesium sulfate, filtered and concentrated in vacuo to yield a solid. Purification by silica gel chromatography (eluent 0–20% $CH_3COOC_2H_5$ in $CH_2Cl_2$) yielded 5.85 g (78%) of a solid. All the analytical data confirmed the assigned structure of coupler M-1.

Preparation of Photographic Elements

Dispersions of the couplers were prepared in the following manner: The quantities of each component are found in Table I. In one vessel the coupler, stabilizer (2, 2'3, 3'-tetrahydro-3, 3, 3', 3'-tetramethyl-5, 5', 6, 6'-tetrapropoxy- 1, 1'-spirobi[1-H-indene]), coupler solvent (diethyl dodecanamide), and ethyl acetate were combined and warmed to dissolve. In a second vessel, gelatin, Alkanol XC™ (surfactant and Trademark of E. I. DuPont Co., USA) and water were combined and warmed to about 40° C. The two mixtures were mixed together and passed three times through a Gaulin colloid mill. The ethyl acetate was removed by evaporation and water was added to restore the original weight after milling.

TABLE I

| Dispersion Number | Coupler Number | Coupler Grams | Stabilizer Grams | Coupler Solvent Grams | Ethyl Acetate Grams | 12.5% Gelatin Grams | Alkanol-XC (10%) Grams | Grams of Water |
|---|---|---|---|---|---|---|---|---|
| 1 | M-1 | 0.889 | 0.444 | 1.333 | 2.666 | 17.76 | 2.22 | 11.69 |
| 2 | M-2 | 0.861 | 0.430 | 1.291 | 2.582 | 19.20 | 2.40 | 13.24 |
| 3 | C-1 | 0.746 | 0.373 | 1.119 | 2.239 | 17.76 | 2.22 | 12.54 |

The photographic elements were prepared by coating the following layers in the order listed on a resin-coated paper support:

| 1st Layer | |
|---|---|
| Gelatin | 3.23 g/m² |
| 2nd Layer | |
| Gelatin | 1.61 g/m² |
| Coupler Dispersion | 4.3 × 10⁻⁷ mole coupler/m² |
| Green-sensitized AgCl emulsion | 0.17 mg Ag/m² |
| 3rd Layer | |
| Gelatin | 1.33 g/m² |
| 2-(2H-benzotriazol-2-yl)-4,6-bis-(1,1-dimethylpropyl)phenol | 0.73 g/m² |
| Tinuvin 326 ™ (Ciba-Geigy) | 0.13 g/m² |
| 4th Layer | |
| Gelatin | 1.40 g/m² |
| Bis(vinylsulfonylmethyl)ether | 0.14 g/m² |

Exposing and Processing of Photographic Elements:

The photographic elements were given stepwise exposures to green light and processed as follows at 35° C.:

| Developer | 45 seconds |
|---|---|
| Bleach-Fix | 45 seconds |
| Wash (running water) | 90 seconds |

The developer and bleach-fix were of the following compositions:

| Developer | |
|---|---|
| Triethanolamine | 12.41 g |
| Blankophor REU ™ (Mobay Corp.) | 2.30 g |
| Lithium polystyrene sulfonate (30%) | 0.30 g |
| N,N-Diethylhydroxylamine (85%) | 5.40 g |
| Lithium sulfate | 2.70 g |
| N-{2-[(4-amino-3-methylphenyl)ethylamino]ethyl}-methanesulfonamide, sesquisulfate | 5.00 g |
| 1-Hydroxyethyl-1,1-diphosphonic acid (60%) | 0.81 g |
| Potassium carbonate, anhydrous | 21.16 g |
| Potassium chloride | 1.60 g |
| Potassium bromide | 7.00 g |
| Water to make | 1.00 L |
| pH @ 26.7° C. adjusted to 10.4 +/− 0.05 | |

| Bleach-Fix | |
|---|---|
| Solution of Ammonium thiosulfate (56.4%) plus Ammonium sulfite (4%) | 127.40 g |
| Sodium metabisulfite | 10.00 g |
| Acetic acid (glacial) | 10.20 g |
| Solution of Ammonium ferric ethylenediaminetetraacetate (44%) + Ethylenediaminetetraacetic acid (3.5%) | 110.40 g |
| Water to make | 1.00 L |
| pH @ 26.7° C. adjusted to 6.7 | |

The invention has been described in detail with particular reference to preferred embodiments thereof, but it will be understood that variations and modifications can be effected within the spirit and scope of the invention.

COMPARISON EXAMPLE

The following examples are used as comparison to illustrate the improvement in Dmax, hue and image-dye light stability achieved with the couplers of the present invention.

Comparative Coupler C-1:

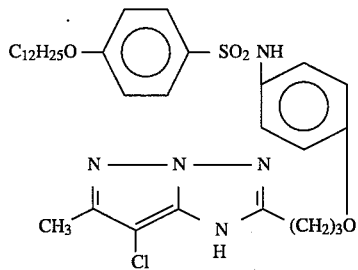

Comparative Coupler C-2:

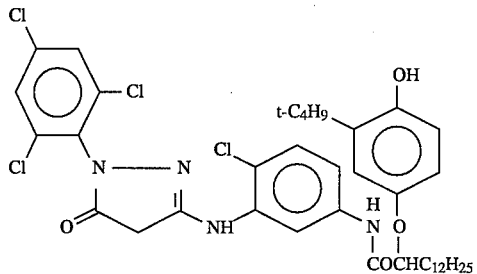

Photographic Tests

Magenta dyes were formed upon processing. The following photographic characteristics were determined: $D_{MAX}$ (the maximum density to green light; Lambda-Max (the wavelength of peak absorption at a density of 1.0); and the Bandwidth (the width of the absorption spectrum in nanometers at the mid-height of the peak density). These values for each example are tabulated in Table II. The data were obtained from two experiments, separated by the double line in Table II.

These data are found in Table III. The data were obtained from two experiments, separated by the double line in Table III.

TABLE III

| Example Number | Dispersion Number | Coupler Number | T30 (Weeks) |
|---|---|---|---|
| 1 | 1 | M-1 (Invention) | 3.33 |
| 2 | 3 | C-1 (Comparative) | 2.17 |
| 3 | 4 | C-2 (Comparative) | 1.32 |
| 4 | 2 | M-2 (Invention) | 3.76 |
| 5 | 4 | C-2 (Comparative) | 1.33 |

The data in tables II and III indicate clearly the couplers of this invention offer comparable or higher D-max, narrower bandwidth and much better image-dye light stability than the comparative couplers.

The invention has been described in detail with particular reference to the preferred embodiments thereof, but, it will be understood that variations and modifications can be effected within the spirit and scope of the invention.

What is claimed is:

1. A photographic element comprising a support bearing at least one photographic silver halide emulsion layer and a dye-forming bicyclic pyrazolo-based coupler, wherein the coupler is represented by formula (III):

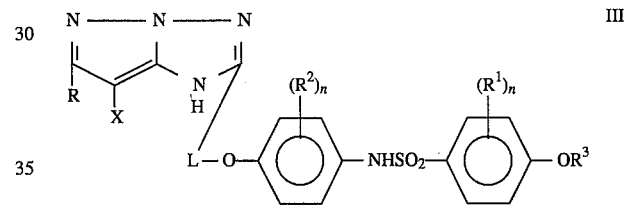

wherein:

R is selected from the group consisting of t-butyl, t-octyl, t-pentyl, and adamantyl;

L is a substituted or unsubstituted alkylene, arylene or aryloxylene group;

$R^1$ and $R^2$ are independently a substituent with each n being from 0 to 4;

$R^3$ is a substituted or unsubstituted alkyl group of at least

TABLE II

| Example Number | Dispersion Number | Coupler Number | $D_{Max}$ Value | $D_{Min}$ Value | Lambda-Max Value | Bandwidth (Nanometers) |
|---|---|---|---|---|---|---|
| 1 | 1 | M-1 (Invention) | 2.42 | 0.08 | 547 | 88 |
| 2 | 3 | C-1 (Comparative) | 2.39 | 0.08 | 544 | 102 |
| 3 | 4 | C-2 (Comparative) | 2.36 | 0.08 | 539 | 106 |
| 4 | 2 | M-2 (Invention) | 2.55 | 0.10 | 546 | 91 |
| 5 | 4 | C-2 (Comparative) | 2.57 | 0.11 | 540 | 106 |

Dispersion 4 was composed of comparison coupler C-2 (8.73% by weight), 3,4-dihydro-2,2-dimethyl-4-(1-methylethyl)- 7-octyl-2H-1-benzopyran-6-ol (3.714%), 2,5-di-sec-dodecylhydroquinone (0.873%), dibutyl phthalate (4.454%), and gelatin (8.69%).

Additional coatings prepared and processed as described above were illuminated by simulated daylight at 50 klux for periods of 2, 4 and 6 weeks. The green densities were monitored and the time in weeks required for 30% density loss from an initial density of 1.0 (T30) was calculated.

10 carbon atoms; and

X is hydrogen or a coupling-off group.

2. A photographic element as in claim 1, wherein each n is 0.

3. A photographic element as in claim 1, wherein the total carbon atoms in R and $R^1$ through $R^3$ is at least 16.

4. A photographic element as in claim 3, wherein L is an alkylene group.

5. A process of forming a dye image in an exposed photographic element comprising a support bearing at least one photographic silver halide emulsion layer, said process comprising developing the photographic element with a color silver halide developing agent in the presence of a color coupler wherein the coupler is represented by formula (III):

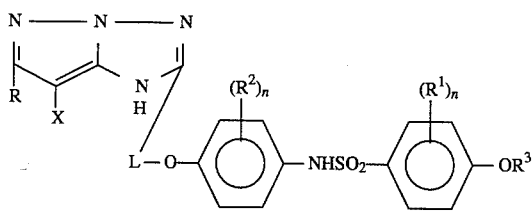

III wherein:

R is selected from the group consisting of t-butyl, t-octyl, t-pentyl and adamantyl;

L is a substituted or unsubstituted alkylene, arylene or aryloxylene group;

$R^1$ and $R^2$ are independently a substituent with each n being from 0 to 4;

$R^3$ is a substituted or unsubstituted alkyl group of at least 10 carbon atoms; and X is hydrogen or a coupling-off group.

6. A photographic element comprising a support bearing at least one photographic silver halide emulsion layer and a dye-forming bicyclic pyrazolo-based coupler, wherein the coupler is represented by formula (III):

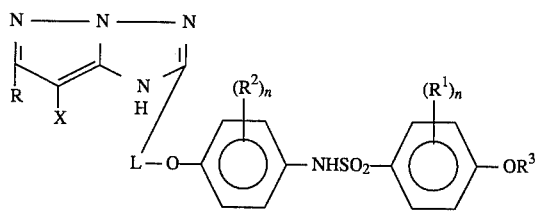

III wherein:

R is selected from the group consisting of t-butyl, t-octyl, t-pentyl, and adamantyl;

L is a divalent linking group;

$R^1$ and $R^2$ are independently a substituent with each n being from 0 to 4;

$R^3$ is a substituted or unsubstituted alkyl group of at least 10 carbon atoms; and X is hydrogen or a coupling-off group.

7. A photographic element as in claim 6, wherein each n is 0.

8. A photographic element as in claim 6, wherein L is selected from the group consisting of a substituted or unsubstituted alkylene, arylene, and aryloxylene group.

9. A photographic element as in claim 6, wherein the total carbon atoms in R and $R^1$ through $R^3$ is at least 16.

10. A photographic element as in claim 6 wherein L is an alkylene group.

* * * * *